United States Patent [19]

Clemence et al.

[11] Patent Number: 4,987,140
[45] Date of Patent: Jan. 22, 1991

[54] PYRIDINES

[75] Inventors: Francois Clemence, Paris; Odile Le Martret, both of Paris; Francoise Delevallee, Fontenay-sous-Bois, all of France

[73] Assignee: Roussel Uclaf, Paris, France

[21] Appl. No.: 441,317

[22] Filed: Nov. 27, 1989

Related U.S. Application Data

[62] Division of Ser. No. 167,375, Mar. 31, 1988, Pat. No. 4,925,859.

[30] Foreign Application Priority Data

Mar. 13, 1987 [FR] France .................. 87 03465

[51] Int. Cl.$^5$ .................. C07D 401/12; C07D 213/56; A61K 31/505; A61K 31/44
[52] U.S. Cl. ..................... 514/335; 514/340; 514/341; 514/346; 544/328; 544/331; 546/261; 546/275; 546/276; 546/278; 546/291; 546/292
[58] Field of Search ............ 546/261, 275, 276, 278, 546/291, 292; 544/328, 331; 514/335, 340, 341, 346

[56] References Cited

U.S. PATENT DOCUMENTS 3,637,714 1/1972 Carlsson et al. ............ 546/261
4,332,809 6/1982 Honma et al. ............. 514/340
4,925,859 5/1990 Clemence et al. ............ 546/276

FOREIGN PATENT DOCUMENTS 6104883 1/1980 Japan ..................... 546/276

Primary Examiner—John M. Ford
Assistant Examiner—Lenora Miltenberger
Attorney, Agent, or Firm—Bierman & Muserlian

[57] ABSTRACT

Novel pyridines of the formula

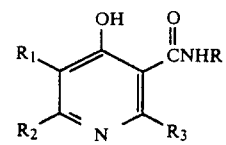

wherein R is selected from the group consisting of (a) phenyl optionally substituted with at least one member of the group consisting of hydroxy, alkyl and alkoxy of 1 to 5 carbon atoms, halogen —CF$_3$ and —NO$_2$ and (b) a 5 to 6 member heterocyclic optionally substituted with alkyl of 1 to 5 carbon atoms, R$_1$ and R$_2$ are individually selected from the group consisting of (a) alkyl of 1 to 5 carbon atoms, (b) 5 to 6 member heterocyclic optionally substituted with alkyl of 1 to 5 carbon atoms and (c) phenyl and naphthyl optionally substituted with at least one member of the group consisting of hydroxy, alkyl and alkoxy of 1 to 5 carbon atoms, halogen, —NO$_3$ and —CF$_3$, R$_3$ is selected from the group consisting of hydrogen, alkyl of 1 to 5 carbon atoms, —(CF$_2$)$_n$ —CF$_3$ and

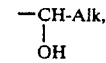

n is an integer from 0 to 4 and Alk is alkyl of 1 to 5 carbon atoms and their non-toxic, pharmaceutically acceptable salts with acids and bases having anti-inflammatory and anti-rheumatic properties.

15 Claims, No Drawings

PYRIDINES

PRIOR APPLICATION

This application is a division of U.S. patent application Ser. No. 167,375 filed Mar. 31, 1988, now U.S. Pat. No. 4,925,859.

STATE OF THE ART

Related pyridines are described in British Pat. No. 2,171,097; U.S. Pat. No. 4,299,381 and French Pat. No. 2,537.140.

OBJECTS OF THE INVENTION

It is an object of the invention to provide the novel compounds of formula I and their non-toxic, pharmaceutically acceptable salts and a process for their preparation.

It is another object of the invention to provide novel anti-inflammatory and anti-rheumatic compositions and a novel method of combatting inflammation and rheumatic conditions in warm-blooded animals.

These and other objects and advantages of the invention will become obvious from the following detailed description.

THE INVENTION

The novel compounds of the invention are selected from the group consisting of pyridines of the formula

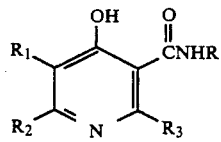

wherein R is selected from the group consisting of (a) phenyl optionally substituted with at least one member of the group consisting of hydroxy, alkyl and alkoxy of 1 to 5 carbon atoms, halogen, $-CF_3$ and $-NO_2$ and (b) a 5 to 6 member heterocyclic optionally substituted with alkyl of 1 to 5 carbon atoms, $R_1$ and $R_2$ are individually selected from the group consisting of (a) alkyl of 1 to 5 carbon atoms, (b) 5 to 6 member heterocyclic optionally substituted with alkyl of 1 to 5 carbon atoms and (a) phenyl and naphthyl optionally substituted with at least one member of the group consisting of hydroxy, alkyl and alkoxy of 1 to 5 carbon atoms, halogen, $-NO_3$ and $-CF_3$, $R_3$ is selected from the group consisting of hydrogen, alkyl of 1 to 5 carbon atoms, $-(CF_2)_n-CF_3$ and

n is an integer from 0 to 4 and Alk is alkyl of 1 to 5 carbon atoms and their non-toxic, pharmaceutically acceptable salts with acids and bases.

When $R_1$, $R_2$ and $R_3$ is alkyl, they are preferably methyl or ethyl, but they may also be n-propyl, isopropyl, n-butyl, isobutyl, tert.-butyl or n-pentyl.

When R is heterocyclic of 5 or 6 links, it is preferably thiazolyl, 4,5-dihydrothiazolyl, pyridinyl, oxazolyl, isoxazolyl, imidazolyl, pyrimidyl or tetrazolyl. When these heterocyclic radicals are substituted by alkyl, it is preferably methyl or ethyl.

When R is substituted phenyl, and when $R_1$ and $R_2$ are substituted phenyl or naphthyl, it is preferably a substituent selected from the group consisting of methyl, ethyl, ethoxy and trifluoromethyl, halogen such as chlorine, fluorine, bromine or iodine and preferably chlorine.

When $R_3$ is $-(CF_2)_nCF_3$, n is preferably 0, 1 or 2. When $R_1$ and $R_2$ are a heterocyclic, it is preferably pyridinyl or thienyl. When this radical is substituted with alkyl, it is preferably methyl or ethyl.

The addition salts with mineral or organic acids can be, for example, the salts formed with the following acids: hydrochloric acid, hydrobromic acid, nitric acid, sulfuric acid, phosphoric acid, acetic acid, propionic acid, formic acid, benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acids such as benzene sulfonic acid.

Among the addition salts with bases, there may be cited those formed with the alkali metals such as sodium, potassium and amines, for example, trimethylamine or dimethylamine.

Among the preferred compounds of formula I are those wherein R is thiazolyl, 4,5-dihydrothiazolyl, phenyl or pyridinyl, those wherein $R_3$ is $-CF_3$ or

and Alk is alkyl of 1 to 5 carbon atoms, those wherein $R_1$ and $R_2$ both are phenyl optionally substituted with at least one member of the group consisting of methyl, ethyl, methoxy, ethoxy, halogen and $-CF_3$ and those wherein one of $R_1$ and $R_2$ is methyl and the other is phenyl optionally substituted with at least one member of the group consisting of methyl, ethyl, methoxy, ethoxy, halogen and $-CF_3$ and their non-toxic, pharmaceutically acceptable salts with acids and bases.

Examples of specific preferred compounds of the invention are:
4-hydroxy-5-methyl-6-phenyl-N-(2-thiazolyl)-2-(trifluoromethyl)-3-pyridine carboxamide,
5,6-diphenyl-4-hydroxy-N-(2-thiazolyl)-2-(trifluoromethyl)-3-pyridine carboxamide,
5,6-bis-(4-chlorophenyl)-4-hydroxy-N-(2-thiazolyl)-2-(trifluoro-methyl)-3-pyridine carboxamide,
5,6-diphenyl-4-hydroxy-2-(1-hydroxypropyl)-4-(2-thiazolyl)-3-pyridine carboxamide and their non-toxic, pharmaceutically acceptable salts with acids and bases.

The novel process of the invention for the preparation of the compounds of formula I comprises reacting a compound of the formula

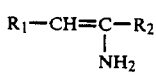

wherein $R_1$ and $R_2$ have the above definitions with an acid of the formula

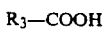

or a functional derivative thereof wherein $R_3$ has the above definition to obtain a compound of the formula

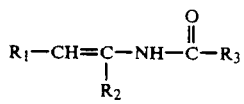

$$R_1-CH=C-NH-\overset{O}{\underset{\|}{C}}-R_3 \quad \text{V}$$
$$\phantom{R_1-CH=C-NH-}R_2$$

reacting the latter with a chlorinating agent to obtain a compound of the formula

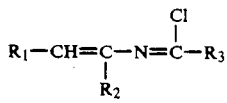

$$R_1-CH=C-N=\overset{Cl}{\underset{|}{C}}-R_3 \quad \text{VI}$$
$$\phantom{R_1-CH=}R_2$$

reacting the latter with an alkyl malonate of the formula $Alk_1OOC-CH_2-COOAlk_1$ wherein $Alk_1$ is alkyl of 1 to 5 carbon atoms in the presence of a strong base to obtain a compound of the formula

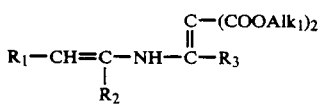

cyclizing the latter to obtain a compound of the formula

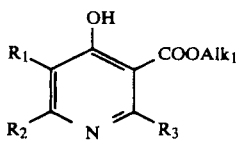

reacting the latter with an amine of the formula $NH_2R$ wherein R has the above definition to obtain the corresponding compound of formula I.

A modification of the process to form the compounds of formula I comprises reacting a compound of the formula

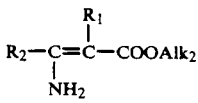

wherein $R_1$ and $R_2$ have the above definition and $Alk_2$ is alkyl of 1 to 5 carbon atoms with an acid of formula IV or a functional derivative thereof to obtain a compound of the formula

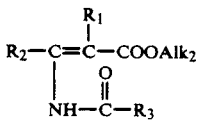

subjecting the latter to hydrolysis to form the corresponding free acid and cyclizing the latter to obtain a compound of the formula

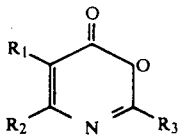

subjecting the latter to an anion of an alkyl acetate of the formula $CH_3-COOAlk_3$, $Alk_3$ being alkyl of 1 to 5 carbon atom to obtain a compound of the formula

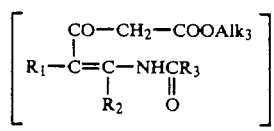

and cyclizing the latter to obtain a compound of formula VIII which is then reacted with an amine of the formula $NH_2-R$ to obtain the compound of formula I.

A variation of the process comprises reacting a compound of formula IX with a compound of the formula $$CH_3-\overset{O}{\underset{\|}{C}}-NH-R \quad \text{XIV}$$

wherein R has the above definition to obtain a compound of the formula $$-\underset{|}{\overset{|}{C}}HAlk$$
$$\phantom{-}OH$$

and cyclizing the latter to obtain the corresponding compound of formula I.

In a preferred mode of the process of the invention, the acid of formula IV is used in the form of its acid anhydride or acid chloride and the reaction with the amine of formula III is effected in the presence of a base such as triethylamine. When $R_3$ is $$\left[\begin{array}{c} COCH_2-CONH-R \\ R_1-C=C-NHCOR_3 \\ R_2 \end{array}\right] \quad \text{XV}$$

in formula I, the acid of formula IV has the hydroxyl protected such as with an alkyl of 1 to 4 carbon atoms, halogen or aryl which is removed after reaction with the amine of the formula $NH_2-R$, for example by reaction with trimethylsilane iodide or boron tribromide preferably.

The chlorinating agent reacted with the compound of formula V is preferably phosphorus pentachloride or a mixture of triphenyl phosphine and carbon tetrachloride. The alkyl malonate is preferably diethyl malonate and the reaction is effected in the presence of sodium hydride.

The cyclization of the compounds of formula VII is preferably effected by heating at 150° to 250°C., for example. The hydrolysis of the compound of formula X may be effected with hydrochloric acid or sodium hydroxide and the corresponding acid may be cyclized in the presence of acetic anhydride or trifluoroacetic anhydride to form the compound of formula XI.

The compound of formula XI may be reacted with the zinc derivative of ethyl bromoacetate in the presence of methylal to obtain the compound of formula XII. The condensation of the compound of formula VIII with the amine of the formula $NH_2R$ is preferably effected in the presence of a base such as sodium hydride or a trialkylaluminium such as trimethylaluminium or triisobutylauminium.

The reaction of the compounds of formulae XI and XIV is preferably effected in the presence of an organo lithium or lithium amide such as in the presence of n-butyllithium or lithium diisopropylamide at low temperatures on the order of −70° C. The cyclization of compounds of formulae XII or XV is effected in the presence of an alkaline agent such as sodium hydride or an alkali metal carbonate such as sodium carbonate or potassium carbonate or potassium tert.-butylate or an amine such as 4-dimethylaminopyridine, piperidine or triethylamine.

The novel anti-inflammatory and anti-rheumatic compositions of the invention are comprised of an anti-inflammatorily and anti-rheumatically effective amount of at least one compound of formula I and its non-toxic, pharmaceutically acceptable addition salts with acids or bases and an inert pharmaceutical carrier or excipient. The compositions may be in the form of tablets, dragees, capsules, granules, suppositories, ointments, creams, gels, injectable solutions or suspensions and aerosol preparations.

The compositions are useful for the treatment of chronic inflammation and certain types of auto-immune diseases and have a peripheral analgesic activity. They are useful for the treatment of degenerative inflammatory diseases such as osteoarthroses, the various collagenoses, (tendinitis, etc. . .) rheumatic diseases (rheumatoid polyarthritis, ankylosing spondyl-arthritis) as well as in the treatment of other disease of an auto-immune nature such as disseminated erythematous lupus, glomerulo-nephritis, disseminated sclerosis as well as in the treatment of psoriasis. They also may be used in the treatment of muscular, articular or nervous pains, dental pains, migraines, and shingles.

Examples of suitable excipients are talc, gum arabic, lactose, starch, magnesium stearate, cocoa butter, aqueous or non-aqueous vehicles, fatty substances of animal or vegetable origin, paraffin derivaties, glycols, the various wetting dispersing or emulsifying agents and preservatives.

Among the preferred compositions are those wherein the active ingredient is selected from the group consisting of
4-hydroxy-5-methyl-6-phenyl-N-(2-thiazolyl)-2-(trifluoromethyl)-3-pyridine carboxamide,
5,6-diphenyl-4-hydroxy-N-(2-thiazolyl)-2-(trifluoromethyl)-3-pyridine carboxamide,
5,6-bis-(4-chlorophenyl)-4-hydroxy-N-(2-thiazolyl)-2-(trifluoromethyl-3-pyridine carboxamide,
5,6-diphenyl-4-hydroxy-2-(1-hydroxypropyl)-4-(2-thiazolyl)-3-pyridine carboxamide,
and their addition salts with pharmaceutically acceptable acids and bases.

The novel method of the invention for treating inflammation and rheumatism in warm-blooded animals, including humans, comprises administering to warm-blooded animals an anti-inflammatorily and anti-rheumatically effective amount of at least one compound of formula I and their non-toxic, pharmaceutically acceptable addition salts with acids and bases. The compounds may be administered orally, rectally, parenterally or topically to the skin and mucosa. The usual effective daily dose is 0.25 to 25 mg/kg depending upon the condition treated, the specific compound and the method of administration.

The starting materials of formula III may be prepared by reacting a compound of the formula

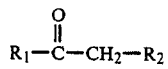

(Tetrahedron Letters 1971 (51) p. 4897) with ammonia in the presence of a titanium salt such as titanium tetrachloride. The starting materials of formula IX are prepared by the process of European Pat. No. 102,318.

The novel intermediates of the invention are the compounds of formula III wherein $R_1$ and $R_2$ are phenyl substituted by methoxy or chlorine, the compounds of formula V when $R_3$ is other than methyl and $R_1$ and $R_2$ are both phenyl, the compounds of formulae XII and XV, and the compounds of formulae VI, VII, VIII, X and the acids of the esters of formulae X and XI except when $R_3$ is methyl.

In the following examples there are described several preferred embodiments to illustrate the invention. However, it is to be understood that the invention is not intended to be limited to the specific embodiments.

EXAMPLE 1

4-hydroxy-5-methyl-6-phenyl-N-(2-thiazolyl)-2-trifluoromethyl-3-pyridine carboxamide STEP A: Ethyl 3-amino-2-methyl-3-phenyl-2-propenoate Under vigorous agitation, 73.2 g of powdered electrolytic zinc were refluxed in 1.2 liter of anhydrous tetrahydrofuran and 10 ml of ethyl 2-bromopropionate were added together with a crystal of sublimed iodine. The reaction started and then, away from reflux, 40.8 ml of benzonitrile were added and the mixture was refluxed which was maintained by the slow addition of 58 ml of ethyl 2-bromopropionate. After cooling, the mixture was poured into 1.5 liters of water containing 200 g of ammonium chloride and extraction was done with ether. The extracts were washed with water, dried, and concentrated under reduced pressure. The residue was taken up with ether and the reduced pressure. The residue was taken up with ether and the insoluble matter was filtered off. The filtrate was concentrated under reduced pressure to obtain 76 g of an unstable product which was used rapidly for the next step.

STEP B: 2-methyl-3-phenyl-3-[(trifluoroacetyl)-amino]-2-propenoic acid 56 ml of trifluoroacetic anhydride were added to 53 g of the product of Step A in 200 ml of pyridine while the temperature was maintained between 20° and 24° C. The solution was poured into a liter of iced water and 110 ml of concentrated hydrochloric acid (pH=1) were added slowly. Extraction was done with ether and the organic phase was washed with water, dried and concentrated to dryness under reduced pressure. The oily residue was added to 400 ml of a saturated aqueous solution of sodium bicarbonate, followed by extraction with ether. The ethereal extracts were washed with water, and the combined aqueous phases were acidified to a pH of 1 with concentrated hydrochloric acid. Extraction was done with ether and the organic phase was washed with water, dried and concentrated to dryness under reduced pressure to obtain 39.3 g of the expected product melting at 140° C.

STEP C:
5-methyl-4-phenyl-2-(trifluoromethyl)-6H-1,3-oxazine-6-one 39.3 g of the product of Step B were refluxed in 80 ml of acetic anhydride and maintained at this temperature for 30 minutes and then allowed to cool. The acetic anhydride was expelled under reduced pressure and iced water was added to the residue. The precipitate obtained was separated, washed abundantly with water and then dissolved in ether. The organic solution was dried and concentrated to dryness under reduced pressure to obtain 34 g of the expected product melting at 70° C.

STEP D:
4-hydroxy-5-methyl-6-phenyl-N-(2-thiazolyl)-2-trifluoromethyl-3-pyridine carboxamide 12.25 g of 2-acetylamino thiazole were cooled to 0° C. in 370 ml of tetrahydrofuran and then 122 ml of a 1.4M solution of n-butyllithium in hexane were added. The mixture was cooled to −70° C. to −75° C., and held at this temperature while adding a solution of 11 g of 5-methyl-4-phenyl-2-(trifluoromethyl)-6H-1,3-oxazine-6-one in 100 ml of tetrahydrofuran. The solution at −70° C. was poured into 700 ml of water and 150 ml of 2N hydrochloric acid. Extraction was done with ether and the extracts were washed with N hydrochloric acid, then with water, dried, and concentrated to dryness under reduced pressure to obtain 24 g of intermediate product. The latter was stirred with 100 ml of tetrahydrofuran and 5.25 g of 4-dimethylamino-pyridine for 1 hour at ambient temperature and 30 minutes at reflux. After cooling, the reaction mixture was poured into 300 ml of water acidified to pH 1 with hydrochloric acid. After extracting with ethyl acetate, washing, drying and concentrating under reduced pressure, 23 g of product were obtained which was taken up in ether. 3.5 g of crystallized product melting at 242° C., corresponding to the 5-methyl-4-phenyl-2-(trifluoromethyl)-2-(thiazolylamino-carbonylmethyl)-6H-1,3-oxazin-6-one separated. A second product slowly crystallized from the ethereal mother liquors and this was separated. The crystals formed were washed with ether to obtain 5.5 g of the expected product. After crystallizing from acetonitrile, 2.8 g of product melted at 256° C.

| Analysis: $C_{17}H_{12}N_3O_2F_3S$; molecular weight = 379.373 |       |       |       |       |       |
| --- | --- | --- | --- | --- | --- |
|  | % C | % H | % N | % F | % S |
| Calculated: | 53.82 | 3.19 | 11.08 | 15.02 | 8.45 |
| Found: | 53.6 | 3.1 | 11.1 | 14.8 | 8.6 |

EXAMPLE 2
2,5-dimethyl-4-hydroxy-6-phenyl-N-(2-thiazolyl)-3-pyridine carboxamide

STEP A: Ethyl 3-(acetylamino)-2-methyl-3-phenyl-2-propenoate 76 g of ethyl 3-amino-2-methyl-3-phenyl-2-propenoate were maintained at 15° C. in 600 ml of tetrahydrofuran and 32.3 ml of pyridine while adding 28.44 ml of acetyl chloride in 100 ml of tetrahydrofuran. The mixture was refluxed for 1 hour, then cooled and poured into a liter of water acidified to pH 1 with 2N hydrochloric acid. After extracting with ether, washing with water, with a saturated solution of sodium bicarbonate and then with water, drying and concentrating to dryness under reduced pressure, 80 g of the expected product were obtained.

STEP B: 3-acetylamino-2-methyl-3-phenyl-2-propenoic acid 80 g of the product of Step A were stirred for 5 hours in 400 ml of isopropanol and 48.5 ml of sodium hydroxide and the solution was poured into a liter of water taken to pH 1 with concentrated hydrochloric acid. The precipitate was separated, washed with water and dried under reduced pressure to obtain 42 g of the expected product melting at 190° C.

STEP C: 2,5-dimethyl-4-phenyl-6H-1,3-oxazin-6-one

Using the procedure of Step C of Example 1, 10 g of the product of Step B was maintained for 2 hours at reflux and the residue was triturated in n-hexane, then separated, washed and dried under reduced pressure to obtain 7.8 g of the expected product which was not very stable in the air and melted at 68° C.

STEP D: 2,5-dimethyl-4-hydroxy-6-phenyl-N-(2-thiazolyl)-3-pyridine carboxamide Using the procedure of Step D of Example 1, 3.3 g of the product of Step C were reacted. Extraction was done with ethyl acetate and the extracts were concentrated under reduced pressure. The residue crystallized slowly and the crystals were triturated in ethyl acetate and separated to obtain 4.5 g of intermediate product which was dissolved in 100 ml of tetrahydrofuran and filtered. The filtrate was concentrated to about 50 ml and precipitated with ether to obtain 2.75 g of impure product. 2.3 g of the latter were taken up in 46 ml of tetrahydrofuran and 1 g of potassium tert-butylate and the mixture was taken progressively to reflux and kept there for 90 minutes. After cooling, the mixture was poured into 100 ml of water with 5 ml of 2N hydrochloric acid, and extracted with a 50—50 mixture of ethyl acetate and tetrahydrofuran, followed by washing with water, drying and concentrating under reduced pressure. The residue was triturated in ether and 1.6 g of product separated which was crystallized successively from ethyl acetate and 96% ethanol to obtain 1.2 g of product melting at 266° C. 1.16 g of the latter was purified by preparing the hydrochloride with 1 ml of a 5.7N solution of hydrochloric acid in ethanol and 1 g of the isolated hydrochloride was stirred in 30 ml of water for 15 minutes at ambient temperature.

The precipitate was separated, washed abundantly with water, and while still humid was dissolved again in 150 ml of tetrahydrofuran. The solution was dried and concentrated to dryness under reduced pressure. The residue was triturated in ether, separated, washed with ether and dried to obtain 735 mg of the expected product melting at 270° C.

| Analysis: $C_{17}H_{15}O_2N_3S$; molecular weight = 325.393 |       |       |       |       |
| --- | --- | --- | --- | --- |
|  | % C | % H | % N | % S |
| Calculated: | 62.75 | 4.65 | 12.91 | 9.85 |
| Found: | 62.9 | 4.7 | 12.7 | 9.6 |

EXAMPLE 3

5,6-diphenyl-4-hydroxy-N-(2-thiazolyl)-2-trifluoromethyl-3-pyridine carboxamide

STEP A: Ethyl 3-amino-(2,3-diphenyl)-2-propenoate

Using the procedure of Step A of Example 1, 59 ml of ethyl α-bromophenyl acetate in toluene were reacted and the ethereal extracts were washed with water, dried and concentrated to dryness to obtain an oily residue of about 70 g which were used as is for the following step.

STEP B:
(2,3-diphenyl-3-(trifluoroacetyl)-amino-2-propenoic acid

Using the procedure of Step B of Example 1, 70 g of the product of Step A were reacted to obtain 36 g of the expected product melting at 175° C.

STEP C:
2-trifluoromethyl-4,5-diphenyl-6H-1,3-oxazin-6-one

Using the procedure of Step C of Example 1, 10 g of the product of Step B were reacted and the residue was triturated in n-hexane, iced, separated, washed and dried under reduced pressure to obtain 7.4 g of the expected product melting at 118° C.

STEP D: Ethyl 5,6-diphenyl-4-hydroxy-2-(trifluoromethyl)-3-pyridine carboxylate Under stirring, 5.88 g of zinc and 60 ml of methylal were mixed together and 1 ml of ethyl bromoacetate and a crystal of iodine were added. The mixture was refluxed and 9.5 g of the product of Step C and 80 ml of methylal were added. Then, while maintaining reflux, 7.3 ml of ethyl bromoacetate and 60 ml of methylal were added. Reflux was maintained for 44 hours and after cooling, the mixture was poured into 300 ml of water containing 50 g of ammonium chloride, then extracted with ether. The organic phase was washed with water, dried and concentrated under reduced pressure to obtain 12 g of product. The latter was dissolved in 200 ml of ether, 50 ml of water and 70 ml of N sodium hydroxide. After decanting, the ethereal phase was washed with water and the combined aqueous phases were acidified to pH 1 with concentrated hydrochloric acid, then extracted with ether, washed with water, dried and concentrated under reduced pressure. The residue was chromatographed on silica to obtain 3.2 g of the expected product melting at 130° C.

STEP E:
5,6-diphenyl-4-hydroxy-N-(2-thiazolyl)-2-trifluoromethyl-3-pyridine-carboxamide 3.22 g of 2-aminothiazole were cooled to +2° C. in 80 ml of methylene chloride, and while maintaining the temperature between +2° and +5° C. 17.9 ml of triisobutyl aluminium in toluene (0.9M) were added and stirred for 20 minutes. 2.5 g of the product of Step D were then introduced all at once into the mixture and the temperature was brought up progressively to reflux and kept there for 24 hours then lowered to the ambient. The mixture was concentrated to dryness under reduced pressure and 50 ml of water and 50 ml of 2N hydrochloric acid were added to the residue. The mixture was triturated and the precipitate was separated and washed abundantly with water. While still humid, the latter was dissolved in tetrahydrofuran and the solution was dried and concentrated under reduced pressure. The 2.6 g of residue were triturated in ether, separated and dried to obtain 2.05 g of product melting at 256° C. After crystallizing from acetonitrile, 1.48 g of the expected product melted at 256° C.

| Analysis: $C_{22}H_{14}N_3F_3O_2S$; molecular weight = 441.44 | | | | | |
|---|---|---|---|---|---|
| | % C | % H | % N | % F | % S |
| Calculated: | 59.86 | 3.20 | 9.52 | 12.91 | 7.26 |
| Found: | 59.8 | 3.1 | 9.4 | 12.7 | 7.3 |

EXAMPLE 4

4-hydroxy-2-trifluoromethyl-N-5,6-triphenyl-3-pyridine carboxamide

Step A: N-(1,2-diphenylethenyl)-trifluoroacetamide 9.8 g of 1,2-diphenylethanone were cooled to 0° C. to 5° C. in 250 ml of a toluene-ether (1-2) mixture and after stirring, ammonia was bubbled in and the temperature was maintained, followed by adding over 30 minutes, 6.85 ml of titanium tetrachloride in 30 ml of an ether-toluene (1-1) mixture. The temperature was allowed to return to ambient and the bubbling in was regulated to maintain it at 20° to 25° C. After 6 hours, the bubbling in was stopped and the mixture was stirred for 16 hours. It was then filtered and washed with ether and the filtrate was concentrated to dryness under reduced pressure to obtain 7.6 g of 1-amino-1,2-(diphenyl)-ethenyl.

26 g of 1-amino-1,2-(diphenyl)-ethenyl was cooled to 0° C. with 130 ml of tetrahydrofuran and 22 ml of triethylamine and 21.67 ml of trifluoroacetic anhydride in 60 ml of tetrahydrofuran were added. The mixture was stirred for 30 minutes while allowing the temperature to return to ambient and was then poured into 500 ml of water, and extracted with ether. The organic phase was washed with water, dried and concentrated to dryness under reduced pressure. The residue was triturated in 100 ml of a (10–90) mixture of isopropyl ether and petroleum ether (b.p. 40° to −70° C.), then separated, washed and dried to obtain 13.8 g of the expected product melting at 148° to 150° C.

Step B: N-[1,2-diphenylethenyl]-trifluoro-ethanimidoyl chloride 18.4 g of the product of Step A were refluxed for 4 hours in 320 ml of methylene chloride, 18.22 g of triphenylphosphine and 6.7 ml of carbon tetrachloride. 9.11 g of triphenylphosphine in 3.35 ml of carbon tetrachloride were added without reflux and after heating for a further one hour at reflux, the mixture stood for 16 hours at ambient temperature. The solvents were expelled under reduced pressure and the residue was triturated in a 1-1 mixture of ether and methylene chloride, then separated. The filtrate was concentrated under reduced pressure and the residue was chromatographed on silica and eluted with methylene chloride to obtain 18.7 g of the expected product.

Step C: Ethyl [1-[(1,2-diphenylethenyl)-imino-2,2,2-trifluoroethyl-propane]dioate]

To 1.4 g of 50% sodium hydride in 15 ml of dimethylformamide, there were added 4.6 ml of ethyl malonate in 15 ml of dimethylformamide while at a temperature between 10° C. and 15° C. and the mixture was stirred for a further 80 minutes at +15° C. 4.5 g of the product of Step B were added in 15 ml of dimethylformamide, followed by stirring for 1 hour at ambient temperature. The mixture was poured into 90 ml of water acidified to pH 1 with hydrochloric acid and extracted with ether. The extracts were washed with water, dried and concentrated under reduced pressure to obtain 10 g of the expected product.

Step D: Ethyl 5,6-diphenyl-4-hydroxy-2-trifluoromethyl-3-pyridine carboxylate 10 g of the product of Step C were stirred vigorously and taken progressively at 220° C. After cooling, the crystals formed were triturated in hexane, iced, separated, washed with hexane, and dried under reduced pressure to obtain 5.2 g of product melting at 130° C.

Step E: 4-hydroxy-2-trifluoromethyl-N-5,6-triphenyl-3-pyridine carboxamide 5.03 g of the product of Step D were stirred in 60 ml of toluene and 3.63 g of aniline and 1.872 g of a 50% dispersion of sodium hydride in oil were added and the mixture was refluxed for 4 hours. At ambient temperature, the mixture was poured into water acidified to pH 1 by hydrochloric acid, then extracted with ether, washed with water, dried and concentrated under reduced pressure to obtain 6 g of residue. The latter was chromatographed on silica and eluted with a 5-95 mixture of ethyl acetate and methylene chloride to obtain 4 g of product which was crystallized from a 1—1 mixture of ether and hexane to obtain 3.76 g of the expected product melting at 172° C.

| Analysis: $C_{25}H_{17}N_2O_2F_3$; molecular weight = 434.426 | | | | |
|---|---|---|---|---|
| | % C | % H | % N | % F |
| Calculated: | 69.12 | 3.94 | 6.45 | 13.12 |
| Found: | 69.3 | 3.9 | 6.4 | 13.4 |

EXAMPLE 5

5,6-diphenyl-4-hydroxy-N-(2-pyridinyl)-2-(trifluoromethyl)-3-pyridine carboxamide 7.05 g of 2-amino-pyridine in 200 ml of methylene chloride were stirred at 10° to 15° C. and 34 ml of tri-isobutylaminium at 1.1 M/l in toluene were added. Stirring was maintained for 30 minutes at 15° C. and then 5.8 g of the product of Step D of Example 4 were added all at once and the mixture was refluxed for 24 hours. The residue was poured into 100 ml of water and 75 ml of 2N hydrochloric acid and stirred for 30 minutes. After separating, the precipitate was washed abundantly with water and dissolved while still humid in tetrahydrofuran. The solution was dried and concentrated to dryness and the residue was triturated in ether and dried under reduced pressure to obtain 5.5 g of product which was crystallized from ethyl acetate to obtain 3.66 g of the expected product melting at 208° to 210° C.

| Analysis: $C_{24}H_{16}N_3O_2F_3$; molecular weight = 435.415 | | | | |
|---|---|---|---|---|
| | % C | % H | % N | % F |
| Calculated: | 66.20 | 3.70 | 9.65 | 13.09 |
| Found: | 66.0 | 3.6 | 9.8 | 12.9 |

EXAMPLE 6

5,6-bis-(4-methoxyphenyl)-4-hydroxy-N-(2-thiazolyl)-2-(trifluoromethyl)-3-pyridine carboxamide Using the procedure of Step E of Example 3, 6.7 g of ethyl 5,6-bis-(4-methoxy-phenyl-4-hydroxy)-2-trifluoromethyl-3-pyridine carboxylate prepared like the product of Step D of Example 4, starting with 1,2-bis-(methoxyphenyl) ethanone were reacted to obtain 5 g of the expected product which after crystallizing from ethyl acetate melted at 230° C.

| Analysis: $C_{24}H_{18}N_3O_4F_3S$; molecular weight = 501.493 | | | | | |
|---|---|---|---|---|---|
| | % C | % H | % N | % F | % S |
| Calculated: | 57.48 | 3.62 | 8.38 | 11.37 | 6.39 |
| Found: | 57.7 | 3.6 | 8.4 | 11.04 | 6.4 |

EXAMPLE 7

5,6-diphenyl-4-hydroxy-N-(4,5-dihydro-2-thiazolyl)-2-(trifluoromethyl)-3-pyridine carboxamide Using the procedure of Step E of Example 3, 5.1 g of 2-amino thiazoline were reacted and the precipitate obtained in suspension in acidified water was extracted with a 6-4 mixture of ethyl acetate and tetrahydrofuran. The organic phase was washed with water, dried and concentrated to dryness under reduced pressure. The residue was triturated with ether, separated and dried under reduced pressure to obtain 3 g of crude product which after crystallizing from acetonitrile yielded 2.5 g of the expected product melting at 280° C.

| Analysis: $C_{22}H_{16}N_3O_2F_3S$; molecular weight = 443.456 | | | | | |
|---|---|---|---|---|---|
| | % C | % H | % N | % F | % S |
| Calculated: | 59.59 | 3.64 | 9.47 | 12.85 | 7.23 |
| Found: | 59.6 | 3.5 | 9.7 | 12.6 | 7.3 |

EXAMPLE 8

5,6-bis-(4-chlorophenyl)-4-hydroxy-N-(2-thiazolyl)-2-(trifluoromethyl)-carboxamide-3-pyridine Using the procedure of Step E of Example 3, ethyl 5,6-bis-(4-chlorophenyl)-4-hydroxy-2-trifluoromethyl-3-pyridine carboxylate was reacted to obtain the expected product melting at 206° to 208° C.

EXAMPLE 9

4-hydroxy-5-phenyl-N-(2-thiazolyl)-6-(2-thienyl)-2-trifluoromethyl-3-pyridine carboxamide.

Step A: N-[2-phenyl-1-(2-thienyl)-ethenyl]-2,2,2-trifluoroacetamide

Using the procedure of Step A of Example 4, 20.2 g of 2-phenyl-1-(2-thienyl) ethanone and 17.38 ml of methylamine were reacted to obtain 8.1 g of the expected product melting at 158° C.

Step B: N-[2-phenyl-1-(2-thienyl)-ethenyl]-2,2,2-trifluoroimidoyl chloride

Using the procedure of Step B of Example 4, 11.2 g of the product of Step A were reacted to obtain 11.8 g of the expected product melting at less than 50° C.

Step C: Diethyl 1-[[1,2-bis-(4-chlorophenyl)-ethenyl]-imino]-2,2,2-trifluoromethyl]-propanedioate Using the procedure of Step C of Example 4, 11.8 g of the product of Step B and 12.5 ml of diethyl malonate were reacted to obtain 25.4 g of the expected product melting at 136° C.

Step D: Ethyl 4-hydroxy-5-phenyl-6-(2-thienyl)-2-(trifluoromethyl)-3-pyridine carboxylate Using the procedure of Step D of Example 4, 25.4 g of the product of Step C were reacted to obtain 12 g of the expected product melting at 136° C.

Step E: 4-hydroxy-5-phenyl-N-(2-thiazolyl)-6-(2-thienyl)-2-trifluoromethyl-3-pyridine carboxamide Using the procedure of Example 5, 10 g of amino thiazol and 6.9 g of the product of Step D were reacted to obtain 5.8 g of the expected product which was crystallized from acetonitrile melting at 260°–262° C.

| Analysis: $C_{20}H_{12}N_3O_2F_3S_2$; molecular weight = 447.466 | | | | | |
|---|---|---|---|---|---|
| | % C | % H | % N | % F | % S |
| Calculated: | 53.68 | 2.70 | 9.39 | 12.74 | 14.33 |
| Found: | 53.6 | 2.6 | 9.4 | 12.7 | 14.0 |

EXAMPLE 10

4-hydroxy-6-methyl-5-phenyl-N-(2-thiazolyl)-2-trifluoromethyl-3-pyridine carboxamide

Step A: Ethyl α-[1-[(trifluoroacetyl)-amino]-ethylidene]-benzene acetate

A mixture of 18.8 g of powdered zinc and 400 ml of tetrahydrofuran was refluxed and 4 ml of ethyl α-bromophenyl acetate were added rapidly. The reaction was initiated and then, away from reflux, 10.4 ml of acetonitrile were added. Reflux was maintained by the slow addition of 42.4 ml of ethyl α-bromophenyl acetate, and when the addition was finished, reflux was maintained for a further thirty minutes. The mixture was then poured at ambient temperature into a solution of 100 g of ammonium chloride in 750 ml of water, and the mixture was extracted with ether. The extracts were washed with water, dried and concentrated to dryness under reduced pressure to obtain 50 g of an oil to which 120 ml of pyridine were added. The mixture was stirred at +10° to +15° C., and 31.14 ml of trifluoroacetic anhydride were added slowly. The mixture was poured into 500 g of ice and 150 ml of concentrated hydrochloric acid, then was extracted with ether. The extracts were washed with water, dried and concentrated to dryness under reduced pressure to obtain 62 g of an oil which was purified by chromatography on silica (methylene chloride - hexane 3–7) to obtain 35.5 g of the expected product.

Step B: α-[1-[(trifluoroacetyl)-amino]-ethylidene]-benzene acetic acid 16.5 g of the product of Step A were dissolved in 15.6 ml of trimethylsilane iodide and after 16 hours of reflux, the solution was poured into 200 ml of a solution of sodium bisulfite and then was extracted with ether. The extracts were washed with water, dried and concentrated to dryness under reduced pressure to obtain 11.7 g of the expected product which after crystallization from heptane melted at 174° C.

Step C: N-(1methyl-2-phenylethenyl)-2,2,2-trifluoroacetamide

To 11.7 g of the product of Step B, 60 ml of quinoline and 600 mg of copper chromite were added and the mixture with vigorous stirring was plunged into a metallic bath heated to 230° to 240° C. for 10 minutes. The mixture was cooled and filtered, and the filtrate was taken up in ether, washed with normal hydrochloric acid and then with water, dried and concentrated under reduced pressure to obtain 9.8 g of the expected product.

Step D: N-(1-methyl-2-phenylethenyl)-2,2,2-trifluoroethanimidoyl chloride

Using the procedure of Step B of Example 4, 9.8 g of the product of Step C were reacted to obtain 10.5 g of the expected product.

Step E: Ethyl [1-[(1-methyl-2-phenylethenyl)-2,2,2-trifluoroethanimidoyl]-propanedioate Using the procedure of Step C of Example 4, 10.5 g of the product of Step D were reacted to obtain 25 g of the expected product.

Step F: Ethyl 4-hydroxy-6-methyl-5-phenyl-2-(trifluoromethyl)-3-pyridine-carboxylate Using the procedure of Step D of Example 4, 25 g of the product of Step E were reacted to obtain 5 g of the expected product melting at 82° to 84° C.

Step G: 4-hydroxy-6-methyl-5-phenyl-N-(2-thiazolyl)-2-trifluoromethyl-3-pyridine-carboxamide Using the procedure of Example 5, 6.25 g of 2-aminothiazole and 4 g of the product of Step F were reacted to obtain 3.7 g of the expected product melting greater than 260° C. after crystallizing from acetonitrile.

| Analysis: $C_{17}H_{12}N_3O_2F_3S$ | | | | | |
|---|---|---|---|---|---|
| | % C | % H | % N | % F | % S |
| Calculated: | 53.82 | 3.19 | 11.08 | 15.02 | 8.45 |
| Found: | 53.7 | 3.1 | 11.0 | 14.7 | 8.5 |

EXAMPLE 11

5,6-diphenyl-4-hydroxy-N-(2-thiazolyl)-3-pyridine carboxamide

Step A: Ethyl 5,6-diphenyl-4-hydroxy-3-pyridine-carboxylate 15 g of 1,2-bis-phenylethanone were heated to reflux in 200 ml of xylene with 1.5 g of p-toluene sulfonic acid and 18 g of diethyl aminomethylene propanedioate were added in two lots. Reflux was maintained for 20 minutes, followed by cooling, pouring into water, and extracting with ethyl acetate. The extracts were dried and concentrated under reduced pressure to obtain 30 g of crude product which was chromatographed on silica (eluent:ethyl acetate - n-hexane, 8-2) to obtain 1.8 g of the expected product melting at 220° C.

Step B: 5,6-diphenyl-4-hydroxy-N-(2-thiazolyl)-3-pyridine carboxamide

Using the procedure of Example 5, 2.5 g of 2-aminothiazole and 1.6 g of the product of Step A were reacted to obtain 1.2 g of the expected product melting greater than 260° C. after crystallizing from acetonitrile.

| Analysis: $C_{21}H_{15}N_3O_2S$; molecular weight = 373.437 | | | | |
|---|---|---|---|---|
| | % C | % H | % N | % S |
| Calculated: | 67.54 | 4.05 | 11.25 | 8.59 |
| Found: | 67.4 | 3.9 | 11.2 | 8.5 |

EXAMPLE 12

5,6-diphenyl-4-hydroxy-2-(1-hydroxypropyl)-N-(2-thiazolyl)-3-pyridine carboxamide

Step A: 1-amino-1,2-(diphenyl)-ethenyl

Using the procedure of Step A of Example 4, 39.2 g of 1,2-diphenylethanone were reacted to obtain 39 g of the expected product.

Step B: N-(1,2-diphenylethenyl)-2-methoxy butanamide

To a stirred mixture of 39 g of the product of Step A, 300 ml of tetrahydrofuran and 20 ml of pyridine at 20° C., a solution of 27.3 ml of 2-methoxy butanoic acid chloride in 100 ml of tetrahydrofuran was added. After refluxing for 1 hour, the mixture was poured into 300 ml of a mixture of iced water and 2N hydrochloric acid, and was extracted with ether. The extracts were washed with water and concentrated under reduced pressure to obtain 54 g of oil which was chromatographed on silica (eluent:methylene chloride) to obtain 21 g of the expected product melting at 78° to 80° C.

Step C: N-(1,2-diphenylethenyl)-2-methoxy butanimidoyl chloride

A solution of 21 g of the product of Step B, 300 ml of methylene chloride and 49.5 ml of triethylamine was cooled to −40° C. and at −40° C. a solution of 9.42 g of diphosgene in 90 ml of methylene chloride was added. The residue, after returning the temperature to 20° C. and concentrating the mixture under reduced pressure, was taken up in ether and filtered. The filtrate was concentrated under reduced pressure to obtain 23 g of the expected product.

Step D: Ethyl [1-(1,2-diphenylethynylimino)-2-methoxybutyl]propanedioate

Using the procedure of Step C of Example 4, 23 g of the product of Step C, 27 ml of ethyl malonate and 8.2 g of sodium hydride were reacted to obtain 54 g of the expected product.

Step E: Ethyl 5,6-diphenyl-4-hydroxy-2-(1-methoxypropyl)-3-pyridine carboxylate Using the procedure of Step D of Example 4, 54 g of the product of Step D were reacted to obtain 8.2 g of the expected product which after crystallization from ether melted at 210° C.

Step F: 5,6-diphenyl-4-hydroxy-2-(1-methoxypropyl)-N-(2-thiazolyl)-3-pyridine carboxamide Using the procedure of Example 5, 9.3 g of the product of Step E and 12 g of 2-aminothiazole were reacted to obtain 8.65 g of the expected product which after crystallization from ether melted at 236° to 238° C.

Step G: 5,6-diphenyl-4-hydroxy-2-(1-hydroxypropyl)-N-(2-thiazolyl)-3-pyridine-carboxamide A solution of 8.65 g of the product of Step F and 86 ml of methylene chloride was cooled to −70° C. to −60° C. and while maintaining this temperature, 116 ml of a solution of boron tribromide were added. After stirring for 24 hours, the temperature was allowed to return to ambient. The solution was poured into 180 ml of iced water and extracted with methylene chloride. The extracts were washed with water, dried and concentrated under reduced pressure. After chromatography under pressure (methylene-chloride - ethyl acetate 8-2), 4 g of the expected product were obtained which after crystallization from ethyl acetate melted at 232° to 234° C.

| Analysis: $C_{24}H_{21}O_3N_3S$; molecular weight = 431.517 | | | |
|---|---|---|---|
| | % C | % H | % N |
| Calculated: | 66.8 | 4.9 | 9.74 |
| Found (not dried): | 66.7 | 4.8 | 9.5 |

EXAMPLE OF PHARMACEUTICAL COMPOSITIONS

Tablets were prepared containing 50 mg of the product of Example 3 and sufficient excipient of lactose, talc, starch and magnesium stearate for a final tablet of 350 mg.

PHARMACOLOGICAL STUDY

Anti-inflammatory activity: chronic-arthritis with adjuvant (preventative treatment)

In the rat, the injection of Freund type adjuvant in a rear paw causes the rapid appearance of a primary inflammatory lesion in this paw and then, after a latency period of 13 to 15 days, the start up of a secondary arthritic affection, particularly in the other rear paw. The test was carried out on male rats aged 42 to 50 days which received an intra-plantar injection of 0.1 ml of "Freund" type adjuvant (suspension in vaseline oil of 6 mg per ml of killed mycobacterium butyricum). The animals received the product orally from day 0 (day of injection of adjuvant) up to the day before they were killed, which occured on day 17. Control arthritic animals and control normal animals received only the vehicle. The criteria of appreciation of the activity of the substances studied was the increases in volume of the injected rear paws (primary and secondary inflammation) and the non-injected ones (secondary inflammation) by comparison with the average volume of the corresponding paws of normal controls. The $DA_{50}$ was determined, that is to say, the dose which reduced by 50% the increase in volume of the rear paws of the treated animals in comparison with the control animals. The results obtained were as follows:

| Product of Example | $DA_{50}$ in mg/k |
|---|---|
| 1 | 0.3 |
| 3 | 15 |

Various modifications of the products and method of the invention may be made without departing from the spirit or scope thereof and it is to be understood that the invention is intended to be limited only as defined in the appended claims.

What we claim is:

1. A compound selected from the group consisting of pyridines of the formula $$\begin{array}{c} \text{OH} \quad \text{O} \\ R_1 \diagdown \diagup \text{CNHR} \\ R_2 \diagup \text{N} \diagdown R_3 \end{array} \quad \text{I}$$

wherein R is selected from the group consisting of phenyl, pyridinyl, oxazolyl, isoxazolyl, imidazolyl, pyrimidyl or tetrazolyl substituted with alkyl of 1 to 5 carbon atoms, $R_1$ and $R_2$ are individually selected from the group consisting of (a) alkyl of 1 to 5 carbon atoms and (b) phenyl and naphthyl unsubstituted or substituted with at least one member of the group consisting of hydroxy, alkyl and alkoxy of 1 to 5 carbon atoms, halogen, $-NO_3$ and $-CF_3$, $R_3$ is selected from the group consisting of hydrogen, alkyl of 1 to 5 carbon atoms, $-(CF_2)_n-CF_3$ and $$\begin{array}{c} -\text{CH-Alk,} \\ | \\ \text{OH} \end{array}$$

n is an integer from 0 to 4 and Alk is alkyl of 1 to 5 carbon atoms or non-toxic, pharmaceutically acceptable salts thereof.

2. A compound of claim 1 wherein R is selected from the group consisting of phenyl and pyridinyl.

3. A compound of claim 1 wherein $R_3$ is $-CF_3$ or $$\begin{array}{c} -\text{CH-Alk} \\ | \\ \text{OH} \end{array}$$

and Alk is alkyl of 1 to 5 carbon atoms.

4. A compound of claim 1 wherein one of $R_1$ and $R_2$ is methyl and the other is phenyl unsubstituted or substituted with a member of the group consisting of methyl, ethyl, methoxy, ethoxy, halogen and $-CF_3$ or $R_1$ and $R_2$ are both phenyl unsubstituted or substituted with at least one member of the group consisting of methyl, ethyl, methoxy, ethoxy, halogen and $-CF_3$.

5. An anti-inflammatory and anti-rheumatic composition comprising an anti-inflammatorily and anti-rheumatically effective amount of at least one compound of claim 1 and an inert pharmaceutical carrier.

6. A composition of claim 5 wherein R is selected from the group consisting of, phenyl and pyridinyl.

7. A composition of claim 5 wherein $R_3$ is $-CF_3$ or $$\begin{array}{c} -\text{CH-Alk} \\ | \\ \text{OH} \end{array}$$

and Alk is alkyl of 1 to 5 carbon atoms.

8. A composition of claim 5 wherein one of $R_1$ and $R_2$ is methyl and the other is phenyl unsubstituted or substituted with a member of the group consisting of methyl, ethyl, methoxy, ethoxy, halogen and $-CF_3$ or $R_1$ and $R_2$ are both phenyl unsubstituted or substituted with at least one member of the group consisting of methyl, ethyl, methoxy, ethoxy, halogen and $-CF_3$.

9. A method of treating inflammation and rheumatism in warm-blooded animals comprising administering to warm-blooded animals an anti-inflammatorily and anti-rheumatically effective amount of at least one compound of claim 1.

10. A method of claim 9 wherein R is selected from the group consisting of phenyl and pyridinyl.

11. A method of claim 9 wherein $R_3$ is $-CF_3$ or $$\begin{array}{c} -\text{CH-Alk} \\ \text{OH} \end{array}$$

and Alk is alkyl of 1 to 5 carbon atoms.

12. A method of claim 9 wherein one of $R_1$ and $R_2$ is methyl and the other is phenyl unsubstituted or substituted with a member of the group consisting of methyl, ethyl, methoxy, ethoxy, halogen and $-CF_3$ or $R_1$ and $R_2$ are both phenyl unsubstituted or substituted with at least one member of the group consisting of methyl, ethyl, methoxy, ethoxy, halogen and $-CF_3$.

13. A compound of claim 1 wherein R is $-CF_3$.

14. A compound of claim 1 which is selected from the group consisting of 4-hydroxy-2-trifluoromethyl-N,5,6-triphenyl-3-pyridine-carboxamide and 5,6-diphenyl-4-hydroxy-N-(2-pyridinyl)-2-trifluoromethyl-3-pyridine-carboxamide and their non-toxic, pharmaceutically acceptable acid addition salts.

15. The method of claim 9 wherein the active compound is selected from the group consisting of 4-hydroxy-2-trifluoromethyl-N,5,6-triphenyl-3-pyridine-carboxamide and 5,6-diphenyl-4-hydroxy-N-(2-pyridinyl)-2-trifluoromethyl-3-pyridine-carboxamide and their non-toxic, pharmaceutically acceptable acid addition salts.

* * * * *